United States Patent [19]

Barnea

[11] Patent Number: 4,669,103
[45] Date of Patent: May 26, 1987

[54] CT SCANNER WITH ROTATABLE FAN BEAM AND NON-ROTATABLE DETECTOR RING

[75] Inventor: Daniel Barnea, Boston, Mass.
[73] Assignee: Elscint Ltd., Haifa, Israel
[21] Appl. No.: 614,547
[22] Filed: May 29, 1984
[51] Int. Cl.[4] .......................... A61B 6/00; G01N 23/00
[52] U.S. Cl. .......................................... 378/10; 378/11; 378/14
[58] Field of Search .................. 378/10, 11, 14, 19, 378/9

[56] References Cited

U.S. PATENT DOCUMENTS

| | | | |
|---|---|---|---|
| 4,129,783 | 12/1978 | Houston | 378/19 |
| 4,137,455 | 1/1979 | Fetter | 378/19 |
| 4,219,733 | 8/1980 | Tschunt | 378/10 |
| 4,274,005 | 6/1981 | Yamamura | 378/10 |
| 4,289,969 | 9/1981 | Cooperstein et al. | 378/10 |

Primary Examiner—Janice A. Howell
Attorney, Agent, or Firm—Sandler & Greenblum

[57] ABSTRACT

A CT scanner has an X-ray source for producing a fan beam that is rotatable relative to the axis of the scanner in a plane perpendicular to the axis, and a plurality of X-ray detectors mounted in a non-rotatable helical detector ring whose axis is colinear with the scannner axis for reeiving X-rays from the fan beam, the detectors extending 360° around the axis. The detector ring has an inner surface facing the axis of the helix, and the detectors are mounted on the inner surface so that their photosensitive areas face the axis of the helix. At any given axial position of the detector ring, a given group of detectors will have an unobstructed view of certain of the X-ray sources through the space between adjacent leaves of the helix.

19 Claims, 6 Drawing Figures

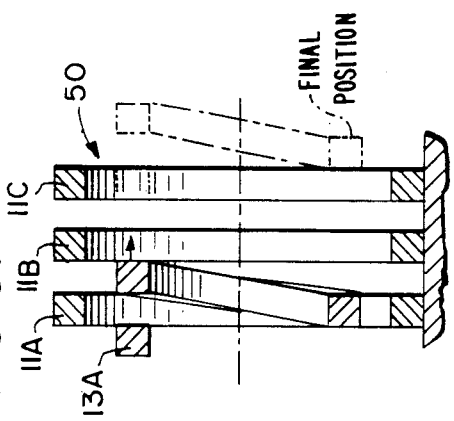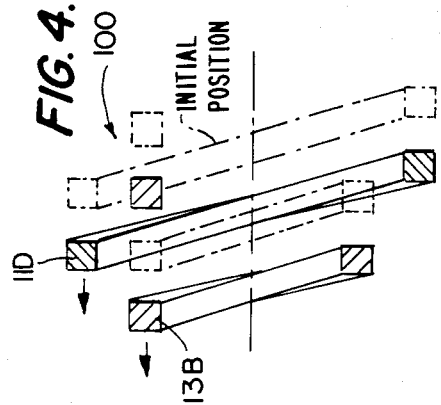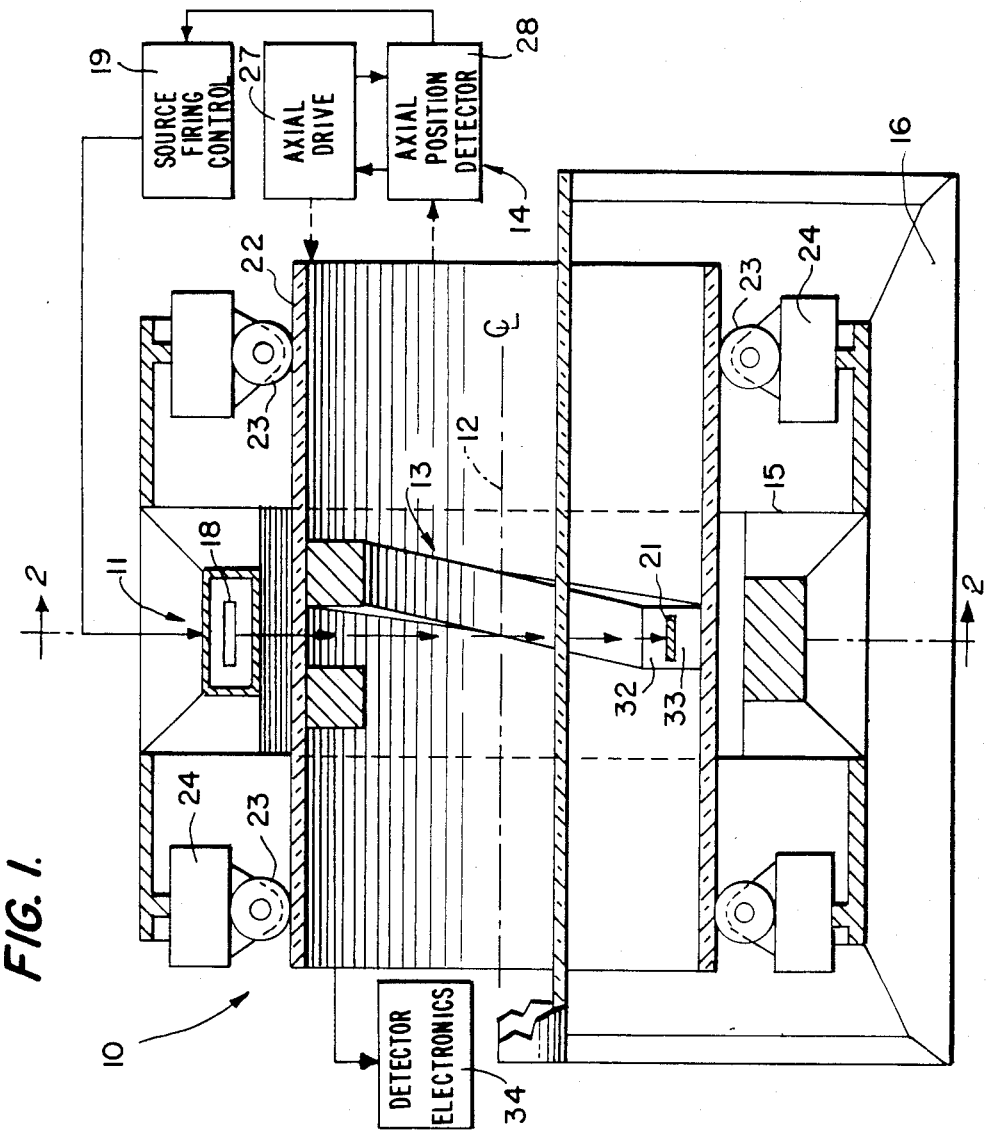

CT SCANNER WITH ROTATABLE FAN BEAM AND NON-ROTATABLE DETECTOR RING

DESCRIPTION

1. Technical Field

This invention relates to a CT scanner with a rotatable fan beam and a non-rotatable detector ring, such scanner being referred to hereinafter as a CT scanner of the type described.

2. Background Art

U.S. Pat. No. 4,137,455 discloses a CT scanner of the type described comprising a conventional X-ray source mounted for 360° rotation about the axis of the scanner and a nutatable detector ring mounted inside the circular path traveled by the source, the detector ring carrying a plurality of detectors extending 360° around the axis. The X-ray source produces a fan beam of radiation in a plane perpendicular to the axis of the scanner; and rotation of the source produces what is termed hereinafter a rotating fan beam whose center lies on the axis. The detector ring is mounted for tilting movement about a ring axis that is normal to the axis of rotation of the fan beam; and the ring axis rotates about the fan beam axis in synchronism with rotation of the source such that the portion of the detector ring adjacent to the source is tilted out of the plane of the fan beam to provide clearance for the fan beam which is incident on the detectors on the detector ring opposite the first mentioned portion.

Because actual rotation of the source is required to establish a rotating fan beam, the time required to complete a scan, even if rotation is limited to 180° and no redundant data are taken, is limited by the acceleration loads that can be tolerated by the rotatable components. When dynamic imaging is involved, i.e., imaging of moving body organs such as a beating heart the temporal constraints on data acquisition imposed by the requirement for the source to complete one revolution produce blurring effects in the reconstructed images.

An attempt to solve this problem is disclosed in U.S. Pat. No. 4,129,783, which discloses a stationary, semicircular array of X-ray sources that are sequentially fired to produce a fan beam of radiation that effectively rotates at a speed determined by the firing rate of the sources, and a stationary, semi-circular array of X-ray detectors positioned to receive the radiation from the rotating fan beam. In this CT scanner of the type described, the rate at which data are acquired is limited only by the time required for the detectors to respond to the incident radiation. Moreover, because the X-ray sources are fired separately, higher power inputs can be tolerated with the result that the X-ray flux produced by each source may be as much as four times greater than that of a conventional, say, 30–50 Kw rotating anode hot cathode X-ray tube which is commonly used in CT scanners. Consequently, for the same patient dose (i.e., the product of X-ray flux and duration of the flux), the last described expedient will permit data acquisition to be achieved in roughly one fourth the time required by a source that actually rotates.

Because rotation of the fan beam in the CT scanner just described is limited to less than 180°, the acquisition of redundant data to improve image quality is not available. Rotation through 360° is required to obtain redundant data; and it has been suggested that the last described expedient could be modified by extending the sources 360° around a fixed source ring, and by substituting a nutating ring containing a 360° array of detectors for the fixed semicircular array. This modification will permit redundant data to be acquired much more rapidly than is possible with a rotating source, but important restraints are nevertheless introduced. First of all, sequential firing of the sources is required in order to accommodate continuous nutation of the detector ring; and this limits the rate at which data can be acquired. Furthermore, sequential firing of the sources means that the same detector will be illuminated sequentially by sequentially fired sources. As a consequence, the rotation speed of the fan beam, i.e., the time period between firing of the sources, is limited to the time required for a detector to recover, which is finite, even with detectors with low after-glow characteristics such as cadmium tungstate. Secondly, there is no possibility of operating this modification in a mode in which a noisier image, but one more rapidly acquired, can be obtained by utilizing less than all the sources (e.g., by utilizing only every other source to establish a more rapidly rotating fan beam) because acceleration loading of the nutating detector ring limits the rotational speed of the fan beam.

By substituting, for the nutating ring described above, an array of detectors mounted on a stationary ring whose axis is colinear with the axis of the scanner but which is non-coplanar with the plane of the fan beam, images can be obtained quickly by skipping some of the sources in completing a scan; or higher quality images can be obtained by using all of the sources. Moreover, the sources can be fired out of sequence to provide time for the detectors to recover. However, these advantages are achieved only by placing the detector ring in a plane that is displaced axially from the plane defined by the rotating fan beam in order to provide clearance for the fan beam. The non-coplanar relationship between the detectors and the fan beam is illustrated in U.S. Pat. No. 4,289,969 which discloses a CT scanner of the type described wherein both the detector ring and the source ring are fixed. The non-coplanarity between the detector ring and the source ring complicates the reconstruction algorithm because account must be taken of the conical nature of the transmission path through the patient. That is to say, the path through the patient traversed by the fan beam when the fan beam rotates through a given 180° of arc is different from the path followed by the fan beam during the remaining 180° of travel. This difference in path adversely affects image quality. Thus, an unsatisfied need exists for a CT scanner of the type described which is capable of rapidly acquiring redundant data; and it is an object of the present invention to provide a new and improved CT scanner of the type described which achieves this end.

BRIEF DESCRIPTION OF INVENTION

The present invention provides a CT scanner of the type described having an X-ray source for producing a fan beam that is rotatable relative to the axis of the scanner in a plane perpendicular to the axis. The scanner also includes a plurality of X-ray detectors mounted in a non-rotatable detector ring whose axis is colinear with the scanner axis for receiving X-rays from the fan beam, the detectors extending at least 360° around the axis.

According to the present invention, the detector ring is constructed in the form of a helix. Specifically, the detector ring has an inner surface facing the axis of the helix, and the detectors are mounted on the inner surface so that their photosensitive area face the axis of the helix. At any given axial position of the detector ring, a given group of detectors will have an unobstructed view of certain of the diametrically opposite X-ray sources through the space between adjacent leaves of the helix. The angular location of the group of detectors that can "see" the sources depends on the axial translational position of the detector helix.

The detector ring is mounted on the scanner for axial displacement which is synchronized with the firing of the sources on the source ring. That is to say, the present invention provides means responsive to the axial position of the detector ring for producing a control signal which is used to control the firing of the sources. The axial position of the detector ring will identify a group of detectors in alignment with the plane of a fan beam originating at an associated source on the source ring having a particular angular or azimuthal position, the group of detectors having a clear view of the source through the leaves of the helix. Axial displacement of the detector ring shifts the azimuthal position of the source associated with the group of detectors aligned with the plane so that displacement of the detector ring through one pitch permits the detectors to "see" all of the sources distributed 360° around the axis of the scanner.

If the pitch of the helix of the detector ring is P, the angular position in degrees of the source that must be fired to generate a fan beam lying in a common plane perpendicular to the axis of the detector ring is given by (360D)/P where D is the axial displacement of the detector ring. Thus, the deviation of the reconstruction plane achieved with the present invention from the desired plane is reduced using a relatively simple arrangement to achieve, linear displacement of the detector ring. Moreover, by sensing the actual position of the detector ring and using the sensed position to trigger firing of the proper source, any nonregularities in the movement will not effect the ability of the system to properly acquire data.

BRIEF DESCRIPTION OF THE DRAWINGS

Embodiments of the present invention are shown in the accompanying drawings wherein:

FIG. 1 is a sectional side view of a CT scanner according to the present invention;

FIGS. 3 and 4 are further embodiments of the source and detector members according to the present invention;

DETAILED DESCRIPTION OF THE DRAWINGS

Figure 2:
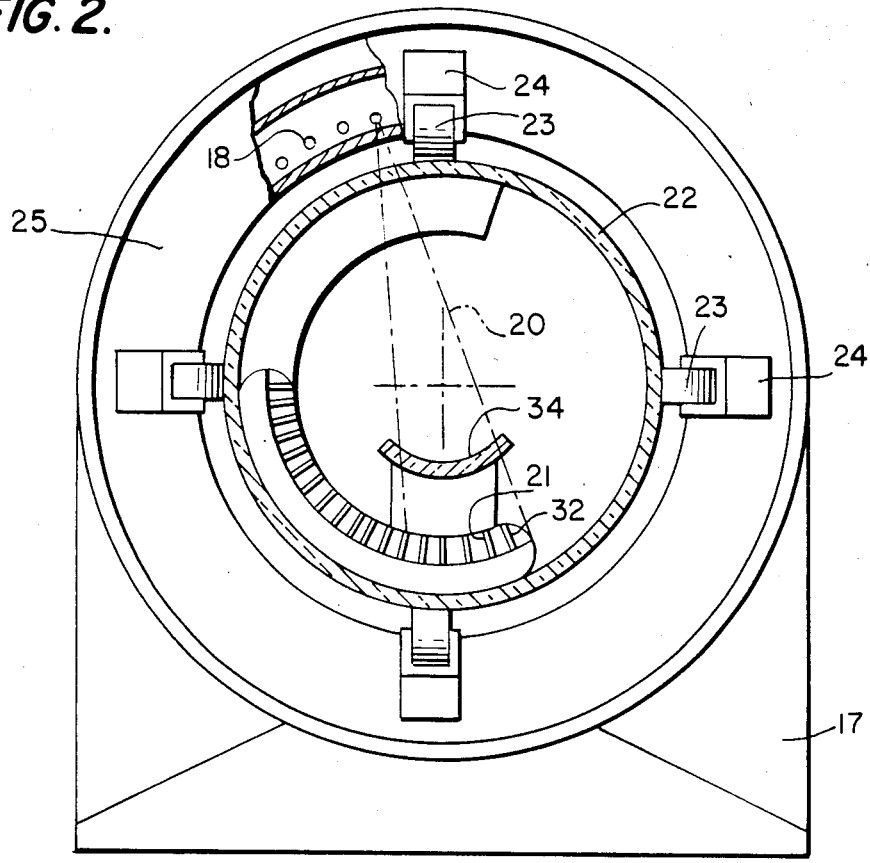
FIG. 2 is a sectional view taken along the line 2—2 of FIG. 1.

Referring now to FIG. 1, reference numeral 10 designates a CT scanner of the type described into which the present invention is incorporated. Scanner 10 comprises circular source member 11 defining axis 12 of the scanner, non-rotatable detector ring member 13 colinear with axis 12, and means 14 for linearly displacing one member relative to the other.

Source member 11 comprises circular housing 15 mounted on base 16 which is provided with suitable supports 17 (FIG. 2) for rigidly holding the housing which contains a plurality of X-ray sources 18 uniformly positioned 360° around axis 12. Sources 18 are schematically shown in the drawings but they may be cold-cathode X-ray sources such as are disclosed in U.S. Pat. No. 4,289,969 for example; or they may be cold-cathode X-ray sources of another type such as disclosed in co-pending application Ser. No. 313,268, filed Oct. 21, 1981. Each of the sources 18 can be fired selectively by firing control circuit 19. That is to say, each of the sources 18 can be fired to produce a fan beam of radiation as suggested by reference numeral 20 in FIG. 2. By sequentially firing sources 18, a rotating fan beam of penetrating radiation can be established, the axis of rotation of the fan beam being axis 12.

Detector ring member 13 includes a plurality of x-ray detectors 21 arranged about the axis of the ring member. Each of the detectors comprises an associated scintillator crystal and photodetector combination 33 for receiving X-rays passing through a circle perpendicular to axis 12, and circumscribed by the outer boundaries of fan beam 20. Detectors 21 are conventional in nature and are not described in detail. There may also exit a fixed concentric collimator 32 inside or outside the detector ring.

The present invention is directed in part toward the arrangement of the X-ray detectors on the detector ring member. Specifically, the detectors are arranged in helical fashion about the axis of the ring member. The inner surface of the detector ring member facing the axis of a helix is defined by the collimators of the detectors so that the scintillator crystals (not shown) face toward axis 12.

Detector ring member 13 is rigidly connected to mounting means 22 for the purpose of establishing the axial position of the detector ring member relative to axis 12. Specifically, mounting means 22 comprises an X-ray transparent tubular sleeve, non-rotatable about axis 12, but axially displaceable therefrom. The sleeve is mounted on guide-rollers 23, rotatably supported on guide blocks 24 attached to frame 25. The tubular sleeve is thus constrained to move only in the axial direction in response to activation of displacing means 14.

The sleeve is positioned at a selected axial position by axial drive 27 which is designed to axially displace detector ring 13 through pitch P (FIG. 1) of the helix at a relative uniform speed. Thus, drive 27 is designed to axially displace the detector ring from rest to its operating speed in a region where the helix is outside the fan beam, to displace the detector ring at a substantially constant speed as the helix moves through the plane of the fan beam, and thereafter, to slow down the detector ring after the helix exits the plane of the fan beam. During displacement of the helix through the plane of the fan beam, the angular or azimuthal position of the detectors that "see" sources 18 through the leaves of the helix will vary through an angle that depends on the total angle of the detectors.

In general, the total angle $\theta$ of the helical array of detectors must equal the sum of the fan beam angle $\phi$ and the total angle of the array of sources. In other words, the sources must be arrayed around the axis through the angle $\theta-\phi$. For example, if the fan beam is 30°, and the sources extend through 180°, then the detectors must extend through 210°.

The displacement means is provided with position detecting arrangement 28 such as photo-electric or magnetic position detectors for the purpose of specifying the axial position of the detector ring, and feeding this information back to the drive. Axial position detecting arrangement 28 thus provides an output for control signals functionally related to the axial position of the sleeve. When applied to firing control 19, a control signal will be effective to fire a selected one of sources 18. As seen in FIG. 1, at a given axial position of the detector ring, a given group of detectors, angularly displaced from the first group, will have an unobstructed view of certain of the X-ray sources through the space between adjacent leaves of the helix as is shown in FIG. 2. As the detector ring moves axially, a different group of detectors will have an unobstructed view of different sources. Thus, when the detector ring has been displaced through a distance equal to the pitch of the helix of the detector ring, the detectors will "see" all of the sources distributed 360° around the axis of the scanner.

Housing 25 provides a rigid mount for table or bed 31, aligned in the axial direction for supporting a body within the circle of reconstruction defined by a circle inscribed within the fan beam and centered on the axis of the scanner.

The output of the photodetectors associated with the detectors mounted in ring 13 is collected and is applied to detector electronics 34 in a conventional manner for obtaining data during a scan. Because no rotation of the detector ring is involved, no slip rings are necessary for obtaining the data produced by the detectors mounted in the detector ring.

In operation, axial drive 27 is effective to bring the detector ring up to its operating speed before the opening in the helix reaches the plane defined by a fan beam produced by sources 18. As the opening in the helix approaches the plane of the fan beam, the axial position of the detector ring will identify a source 18 that will produce a fan beam which will pass between the leaves of the helix and impinge upon a group of detectors on the detector ring. The axial position of the detector ring is sensed by detector 28 and used to signal firing control 19 for the purpose of firing the proper source 18. As the detector ring moves axially, detector 28 produces additional control signals which shift the firing of sources 18 in synchronism with the axial position of the ring. In this way, axial displacement of the detector ring through the pitch of the helix will be sufficient to permit firing of all of the sources.

This arrangement is advantageous over conventional CT scanners of the type described. Only linear displacement of the detector ring is required rather than rotation of a much heavier and more complex source ring. Moreover, because the flux produced by cold-cathode X-ray tubes is approximately four times greater than the flux produced by a conventional hot-cathode anode X-ray tube, information sufficient to produce an image of the same quality as an image produced by a rotating source can be obtained in approximately one fourth the time. That is to say, if a conventional CT scanner of the type described utilizing a rotating x-ray source can obtain data in one second sufficient to produce an image, the device according to the present invention would be capable of producing the same results in about 250 msec. Furthermore, the present invention has a further advantage in that an image can be obtained even faster by speeding up the axial displacement of the detector ring and utilizing say every other source. A more noisier image would be obtained, but it would be obtained faster and would have use for that reason.

Image quality can be improved by utilizing sequentially-progressing bank firing of the sources, which permits the speed of movement of the detector member to be reduced, and the dosage to be increased. The term "sequentially-progressing bank firing" means a system for firing the sources in which firing occurs sequentially until all of the sources in a first group have been fired, and then this sequence is broken off, and firing occurs sequentially in a second group that overlaps the first group. Thus, sequentially-progressing bank firing differs from sequential firing of the sources described previously, which constitutes a special form of sequentially-progressive bank firing in which all of the sources constitute the group.

If the sources are designated by the counting numbers, then regular sequential firing occurs in this sequence: 1, 2, 3, ..., N, where N is the total number of sources, and each source is fired once. On the other hand, sequentiallyprogressing bank firing occurs as follows: 1, 2, 3, ..., n, 2, 3, 4, ..., n+1, 3, 4, 5, ..., n+2, etc., where n constitutes the number of times each source is fired in a complete cycle. Sources 1, 2, 3, ..., n constitute a first group; sources 2, 3, 4, ..., n+2 constitute a second group, etc.

Figure 5:
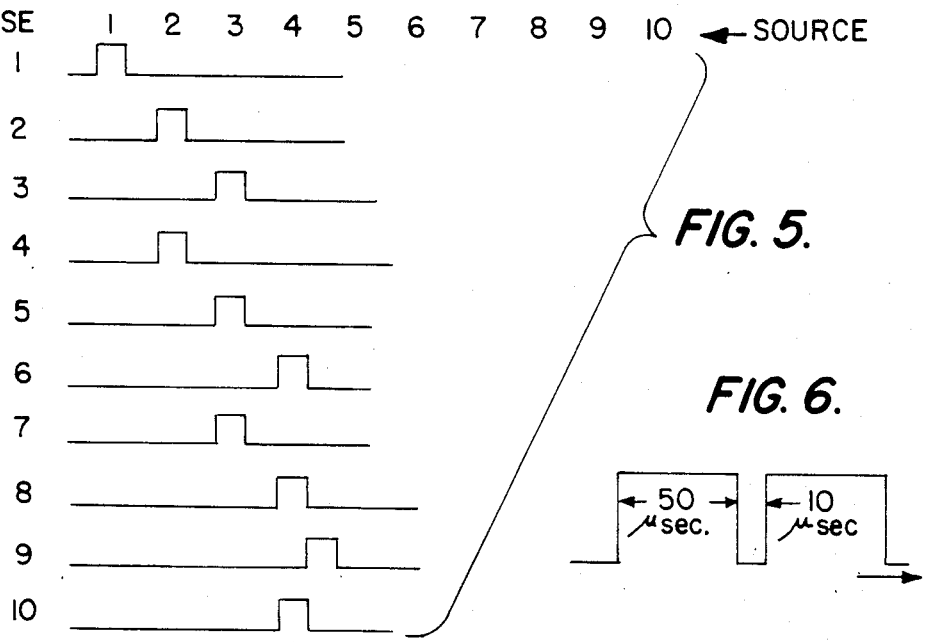
FIG. 5 is a timing diagram that shows sequential bank firing.
Figure 6:
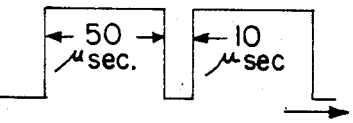
FIG. 6 is a timing diagram that shows the relationship between sequentially-occurring firing pulses.

Sequentially-progressing bank firing is shown in FIG. 5 for n=3. Thus, each source after the second source is fired three times. If the X-ray burst is of 50 usec duration, with a 10 usec interval between bursts, as shown in FIG. 6, the firing scheme is shown in FIG. 5. Thus, the first group of sources is constituted by sources "1-3", the second group by sources "2-4", etc. The source firing control is programmed to sequentially fire sources "1-3" at 60-usec intervals, providing 10-usec intervals between successive bursts of X-rays (see FIG. 6). The second group of sources "2-4" is then fired sequentially in a similar manner, then the third group, etc. As can be seen in FIG. 5, source "3" is fired three times, with the period being 120 usec. In general, the period for multiple firings of the sources is 60(n−1) usec.

In order to obtain multiple slices through a body, scanner 50 as shown in FIG. 3 can be utilized. Scanner 50 includes a plurality of stationary source members 11A, 11B, 11C (each similar to source 11 of FIG. 1), and an axially displaceable helical detector ring 13A (similar to ring 13). In use, detector ring 13A is displaced axially past the three source members to the axial position indicated by the broken lines to permit data to be acquired, in sequence, associated with three axially displaced sections through a body located within the detector ring. In scanner 100 shown in FIG. 4, a single source ring 11D is utilized, but in this case the ring is helical in nature and can be moved axially, independently of helical detector ring 13B, but in synchronism therewith. In scanner 100, the source and detector rings are moved in the same direction for the purpose of obtaining axially displaced slices simultaneously through a patient.

It is believed that the advantages and improved results furnished by the method and apparatus of the present invention are apparent from the foregoing description of the preferred embodiment of the invention. Various changes and modifications may be made without departing from the spirit and scope of the invention as described in the claims that follow.

I claim:
1. In a CT scanner having a non-rotating source ring of X-ray sources producing fan beams of X-rays that rotate relative to the axis of the scanner in a plane per- pendicular to the axis, a plurality of X-ray detectors for detecting the X-rays of the fan beams after passage through a subject, said detectors being mounted in an array on a non-rotatable detector ring whose diameter is smaller than the source ring and whose axis is coaxial with the scanner axis, said array of detectors extending through an angle $\theta$ around the axis, the improvement comprising: the detector ring being in the form of the helix, and means for moving said detector ring and said X-ray source ring axially relative to each other in synchronism with said rotating fan beam so that the fan beam impinges on the detectors on said detector ring in a sequential manner.

2. The invention of claim 1 wherein the detector ring has an inner surface facing the axis of the helix, and the detectors are mounted on said inner surface facing the axis.

3. The invention of claim 2 wherein the detector ring is mounted on the scanner for axial displacement.

4. The CT scanner of claim 1 wherein the X-ray sources on the non-rotating ring extend through an angle of $\theta - \phi$ around the axis where $\phi$ is the fan beam angle, and means for firing the X-ray sources selectively.

5. The invention of claim 4 wherein $\theta$-$\phi$=360°.

6. The invention of claim 4 wherein $\theta$-$\phi$=180°.

7. The invention of claim 4 including means responsive to the axial position of the detector ring for producing a control signal, and means to fire the sources responsive to the control signal.

8. The invention of claim 1 wherein the improvement includes means for detecting the axial position of the detector ring to determine the axial displacement of the detector ring, means responsive to the axial displacement of the detector ring for firing the particular source whose fan beam passes through the subject to impinge on the detectors of the array on said detector ring that are in view of said source unobstructed by said helix as the detectors move axially relative to the sources.

9. A CT scanner comprising:
   (a) a non-rotatable source member for producing a fan beam of penetrating radiation which is rotatable relative to the axis of the scanner in a plane perpendicular to the axis;
   (b) a non-rotatable detector ring member including a plurality of radiation detectors arranged in a helical fashion about the axis of the ring member; and
   (c) means for axially displacing one member relative to the other.

10. A CT scanner according to claim 9 including means for selectly displacing the detector ring along said axis.

11. A CT scanner according to claim 10 wherein the source member is in the form of a stationary ring that includes a plurality of sources of penetrating radiation arrayed about the axis of the scanner, and means are provided for selectively firing the sources.

12. A CT scanner according to claim 11 including means responsive to the axial displacement of the detector ring for selectively firing the sources in synchronism with the displacement.

13. A CT scanner according to claim 12 wherein the source ring is such that the sources define a plane perpendicular to the axis of the scanner.

14. A CT scanner according to claim 10 wherein the source member is in the form of a plurality of non-rotatable rings, each of which includes a plurality of sources of penetrating radiation arranged about the axis of the scanner, and means are provided for selectively firing the sources.

15. A CT scanner according to claim 14 including means responsive to the axial displacement of the detector ring for selectively firing the sources in synchronism with the displacement.

16. A CT scanner according to claim 15 wherein the source rings are such that the sources of penetrating radiation define parallel planes, each of which is perpendicular to the axis of the scanner.

17. A CT scanner comprising:
   (a) a non-rotating array of selectively fireable X-ray sources mounted on a first helix for producing fan beams of X-rays that rotate around the axis of the scanner when said sources are selectively fired;
   (b) a plurality of non-rotatable X-ray detectors for detecting the fan beams after passage through a subject, said detectors being mounted in an array on a second helix that is coaxial with said first helix and with the axis of the scanner, the diameter of the second helix being smaller than the diameter of the first helix, said array of detectors extending through a predetermined angle around the axis;
   (c) means for axially displacing both the first helix and the second helix;
   (d) means for detecting the axial displacement of the first and second helices; and
   (e) firing means operated responsive to the detected axial displacements for firing a particular source whose fan beam is in a first plane which passes through the subject and which impinge on detectors of the detector array that are in view of said particular fired source unobstructed by said second helix as the detectors move axially relative to the sources so that the rotating fan beams which impinge on said subject and are in said first plane are detected.

18. The CT scanner of claim 17 wherein said firing means fires a plurality of sources whose fan beams are in a plurality of planes extending from said sources through said subject to said detectors unobstructed by said second helix so that a plurality of planar views are obtained during the axial movement of the first and second helices.

19. In a CT Scanner having a plurality of sources of penetrating radiation individually and selectively operable for producing a fan beam of radiation in a plane perpendicular to the axis of the scanner, and a plurality of detectors of said penetrating radiation mounted in a non-rotatable detector ring whose axis is colinear with the scanner axis for receiving penetrating radiation from the sources, the improvement comprising: sequentially operating the sources in progressive groups, where there are at least two groups and wherein the sources are operated in the following sequence: 1, 2, 3, . . . , n, 2, 3, 4, . . . , n+1, 3, 4, 5, . . . , n+2 . . . where n constitutes the number of times each source is fired in a complete cycle.

* * * * *